(12) United States Patent
Lee et al.

(10) Patent No.: US 6,872,569 B2
(45) Date of Patent: Mar. 29, 2005

(54) IN VITRO PRODUCTION OF HAPLOID GERM CELLS

(75) Inventors: Dong Ryul Lee, Seoul (KR); Michael T. Kaproth, Ithaca, NY (US); John E. Parks, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 19 days.

(21) Appl. No.: 10/147,576

(22) Filed: May 16, 2002

(65) Prior Publication Data

US 2003/0027329 A1 Feb. 6, 2003

Related U.S. Application Data

(60) Provisional application No. 60/292,032, filed on May 18, 2001.

(51) Int. Cl.$^7$ .............................. C12N 5/06; C12N 5/08; A01N 1/02
(52) U.S. Cl. ........................ 435/373; 435/382; 435/378; 435/383; 435/366; 435/352
(58) Field of Search ................................ 435/373, 382, 435/378, 383, 366, 352

(56) References Cited

U.S. PATENT DOCUMENTS

| | | |
|---|---|---|
| 5,166,190 A | 11/1992 | Mather et al. |
| 5,817,453 A | 10/1998 | Brinster |
| 5,849,285 A | 12/1998 | Selawry |
| 5,858,354 A | 1/1999 | Brinster |
| 5,942,437 A | 8/1999 | Sanberg et al. |
| 5,958,404 A | 9/1999 | Selawry |
| 6,037,175 A | 3/2000 | Cameron et al. |

OTHER PUBLICATIONS

Mather et al. In: "Methods for Serum–Free Culture of Cells of the Endocrine System". Barnes and Sato eds. (Alan R. Liss, Inc.: New York, 1984), pp. 29–45.*
Karl et al., "Sertoli Cells of the Testis: Preparation of Cell Cultures and Effects of Retinoids," *Methods in Enzymology* 190:71–75 (1990).
Dietrich et al., "Testicular Cell Suspensions of the Mouse in vitro," *Andrologia* 15(3):236–246 (1983).
Wright, "Germ Cell–Sertoli Cell Interactions: Analysis of the Biosynthesis and Secretion of Cyclic Protein–2," *Dev. Biol.* 130(1):45–56 (1988) (abstract only).
Li et al., "Spermatogenic Cell–Somatic Cell Interactions are Required for Maintenance of Spermatogenic Cell Glutathione," *Biol. Reprod.* 40(2):317–331 (1989) (abstract only).
Sharpe et al., "Cell–Cell Interactions in the Control of Spermatogenesis as Studied Using Leydig Cell Destruction and Testosterone Replacement," *Am. J. Anat.* 188(1):3–20 (1990) (abstract only).
Kierszenbaum, "Mammalian Spermatogenesis in Vivo and in Vitro: A Partnership of Spermatogenic and Somatic Cell Lineages," *Endocrine Reviews* 15(1):116–134 (1994).

Wright et al., "Germ Cell–Sertoli Cell Interactions: Regulation by Germ Cells of the Stage–Specific Expression of CP–2/Cathespin L mRNA by Sertoli Cells," *Dev. Genet.* 16(2):104–113 (1995) (abstract only).
Weiss et al., "Pre– and Postmeiotic Expression of Male Germ Cell–Specific Genes Throughout 2–Week Cocultures of Rat Germinal and Sertoli Cells," *Biol. of Reprod.* 57:68–76 (1997).
Hue et al., "Meiotic Differentiation of Germinal Cells in Three–Week Cultures of Whole Cell–Population from Rat Seminiferous Tubules," *Biol. of Reprod.* 59:379–387 (1998).
Nayernia et al., "A Novel Testicular Haploid Expressed Gene (THEG) Involved in Mouse Spermatid–Sertoli Cell Interaction," *Biol. Reprod.* 60(6): 1488–1495 (1999) (abstract only).
Kraszucka et al., "Development Stage– and Germ Cell–Regulated Expression of a Calcium–Binding Protein mRNA in Mouse Sertoli Cells," *Mol. Reprod. Dev.* 54(3):232–243 (1999) (abstract only).
Tesarik et al., "In Vitro Differentiation of Germ Cells from Frozen Testicular Biopsy Specimens," *Human Reproduction* 15(8): 1713–1716 (2000).
Tanaka et al., "Clinical Evaluation of Round Spermatid Injection (ROSI) Into Human Oocytes," *American Society of Reproductive Medicine (ASRM) Abstracts, 1996 ASRM Meeting* (1996) (abstract only).
Tesarik et al., "Treatment of Severe Male Infertility by Micromanipulation–Assisted Fertilization: News and Views," *Frontiers in Bioscience* 3:e238–246 (1998).
Silber et al., "Are Round Spermatid Injections of Any Clinical Value? ROSNI and ROSI Revisited," *Human Reproduction* 13(3):509–523 (1998).
Hovatta, "Cryopreservation of Testicular Tissue in Young Cancer Patients," *Human Reproduction Update* 7(4):378–383 (2001).
Staub, "A Century of Research on Mammalian Male German Cell Meiotic Differentiation In vitro," *Journal of Andrology* 22(6): 911–926 (2001).
Lee et al., "Blastocyst Production by Intracytoplasmic Injection of Haploid Germ Cells Derived In vitro from Bovine Neonatal Gonocytes," *Biol. Reprod.* 64(Suppl. 1):131 (2001) (abstract only).

(Continued)

Primary Examiner—Vera Afremova
(74) Attorney, Agent, or Firm—Nixon Peabody LLP (57) ABSTRACT

The present invention relates to a method of in vitro spermatogenesis involving Sertoli cells and diploid germ cells from a testis of a male mammal to yield differentiated haploid spermatids. The present invention also relates to spermatids produced by the method described above, where the spermatids are haploid. The present invention also involves a method of overcoming male infertility in mammals involving the use of the haploid round spermatids produced by the in vitro spermatogenesis method of the present invention. The present invention also relates to isolated haploid spermatids.

21 Claims, 4 Drawing Sheets

OTHER PUBLICATIONS

Lee et al., "In vitro Production of Haploid Germ Cells from Testicular Cells of Neonatal Bulls," *Biol. Reprod.* 62 (Suppl 1) (Jun. 2000) (abstract only).

Lee et al., "In vitro Production of Haploid Germ Cells from Fresh or Frozen–Thawed Testicular Cells of neonatal Bulls," *Biol. Reprod.* 65:873–878 (2001).

* cited by examiner

SEQUENCE LISTING

<160> NUMBER OF SEQ ID NOS: 6

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 1
agaggccgct accactacag acaca                                    25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 2
acttagagct gccttccgca tctcc                                        25

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 3
ggaagagcag cctgaagagt                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 4
tcaggtctcc ttggcagtcc                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 5
acggcacagt caaggcagag                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 6
gtgatggcgt ggacagtggt                                              20

IN VITRO PRODUCTION OF HAPLOID GERM CELLS

This application claims the benefit of U.S. Provisional Patent Application Ser. No. 60/292,032, filed May 18, 2001.

Field of the Invention

The present invention relates to a method of in vitro spermatogenesis.

The present invention also relates to methods of overcoming male infertility of mammals using the in vitro spermatogenesis method of the present invention. The present invention further relates to an isolated haploid spermatid.

BACKGROUND OF THE INVENTION

Spermatogenesis is the process of germ cell proliferation and differentiation within the seminiferous tubules of the testis which leads to a haploid, free-swimming spermatozoon. Orchestrated in large measure by Sertoli cells, spermatogenesis requires complex endocrine and auto/paracrine regulation as well as direct cell-to-cell interaction (Parvinen et al., "Cell Interactions During the Seminiferous Epithelial Cycle," *Int. Rev. Cytol.* 104:115–151 (1986); Kierszenbaum, "Mammalian Spermatogenesis In vivo and In vitro: A Partnership of Spermatogenic and Somatic Cell Lineages," *Endocr. Rev.* 15:116–134 (1994); Griswold, "The Central Role of Sertoli Cells in Spermatogenesis," *Semin. Cell Dev. Biol.* 9:411–416 (1998)). However, precise molecular mechanisms regulating the extensive cross-talk among various somatic and germ cell types remain to be established.

An effective procedure for recapitulating spermatogenesis in vitro would greatly facilitate mechanistic studies of the in vivo process while providing a biological basis for treating selected causes of male infertility and genetically modifying the male germ line. In vitro spermatogenesis (IVS) could be applied to generate developmentally competent haploid spermatids or sperm which could then be used in conjunction with round spermatid injection (ROSI) or intracytoplasmic sperm injection (ICSI) procedures (Palermo et al., "Pregnancies After Intracytoplasmic Sperm Injection of Single Spermatozoon into an Oocyte," *Lancet* 340:17–18 (1992); Van Steirteghem et al., "Use of Assisted Fertilization," *Hum. Reprod.* 8:1784–1785 (1993)) to overcome male factor infertility, especially azoospermia due to maturation arrest (Tesarik et al., "Restoration of Fertility by In-vitro Spermatogenesis," *Lancet* 353: 555–556 (1999)). Also, transfection of diploid germ cells in culture followed by IVS would provide a direct approach to genetic modification of the male germ line (Brinster et al., "Spermatogonial Stem Cell Transplantation, Cryopreservation, and Culture," *Semin. Cell Dev. Biol.* 9: 401–409 (1998)), including targeted gene insertion via homologous recombination.

Devising an IVS culture system that will support germ cell development through meiosis has been especially challenging. Miura et al. reported an organ culture system in which fragments of immature Japanese eel testis, containing only spermatogonia and inactive testicular somatic cells, were maintained and completed spermatogenesis in a chemically defined medium (Miura et al., "Hormonal Induction of All Stages of Spermatogenesis In vitro in the Male Japanese Eel (*Anguilla japonica*)," *Proc. Natl. Acad. Sci. USA* 88: 5774–5778 (1991)). In rodents, some stage-specific progression of spermatogenesis has been achieved in vitro utilizing organ culture or co-culture with immortalized Sertoli cells (Rassoulzadegan et al., "Transmeiotic Differentiation of Male Germ Cells in Culture," *Cell* 75: 997–1006 (1993); Tajima et al., "Insulin-Like Growth Factor-I and Transforming Growth Factor-α Stimulate Differentiation of Type A spermatogonia in Organ Culture of Adult Mouse Cryptorchid Testes," *Int. J. Androl.* 18:8–12 (1995); and Weiss et al., "Pre- and Postmeiotic Expression of Male Germ Cell-Specific Genes Throughout 2-Week Cocultures of Rat Germinal and Sertoli Cells," *Biol. Reprod.* 57: 68–76 (1997)).

Mammalian germ cells can be maintained in culture for months during which they retain their full spermatogenic potential (Brinster et al., "Spermatogonial Stem Cell Transplantation, Cryopreservation, and Culture," *Semin. Cell Dev. Biol.* 9: 401–409 (1998)), but difficulties in establishing conditions for germ cells to proceed to and through meiosis have limited the success of IVS culture systems (Kierszenbaum, "Mammalian Spermatogenesis In vivo and In vitro: A Partnership of Spermatogenic and Somatic Cell Lineages," *Endocr. Rev.* 15:116–134 (1994)). Recently, however, meiosis of rat germ cells in culture has been reported using seminiferous tubule segments (Weiss et al., "Pre- and Postmeiotic Expression of Male Germ Cell-Specific Genes Throughout 2-Week Cocultures of Rat Germinal and Sertoli Cells," *Biol. Reprod.* 57: 68–76 (1997); and Hue et al., "Meiotic Differentiation of Germinal Cells in Three-Week Cultures of Whole Cell Population from Rat Seminiferous Tubules," *Biol. Reprod.* 59:379–387 (1998)). By measuring the expression of stage-specific markers phosphoprotein p19 and testis-specific histone TH2B (pachytene spermatocytes) and transition proteins T1 and T2 (round spermatids) as a function of days in culture, Hue et al. demonstrated an increase in the round spermatid to spermatocyte ratio during a 3-week culture (Hue et al., "Meiotic Differentiation of Germinal Cells in Three-Week Cultures of Whole Cell Population from Rat Seminiferous Tubules," *Biol. Reprod.* 59:379–387 (1998)). The increased ratio corresponded to an increase in haploid cells in culture based on ploidy analysis. Retention of germ cell-Sertoli cell associations during tissue dissociation was considered to be a critical feature of this culture system. Tesarik et al. recently reported a live human birth following ROSI using spermatids recovered after in vitro differentiation of primary spermatocytes (Tesarik et al., "Restoration of Fertility by In-vitro Spermatogenesis," *Lancet* 353: 555–556 (1999)). However, complete IVS from gonocytes through spermatocytogenesis, meiosis, and spermiogenesis has not been reported previously for mammalian species.

The complete recapitulation of spermatogenesis in vitro remains an elusive goal in reproductive biology. While germ cell viability and functionality can be maintained for extended periods in culture (Brinster et al., "Spermatogonial Stem Cell Transplantation, Cryopreservation, and Culture," *Semin. Cell Dev. Biol.* 9: 401–409 (1998)), only limited differentiation of spermatogenic cells has been achieved in vitro (Kierszenbaum, "Mammalian Spermatogenesis In vivo and In vitro: A Partnership of Spermatogenic and Somatic Cell Lineages," *Endocr. Rev.* 15:116–134 (1994)). Several reports in recent years have demonstrated that germ cells cultured in association with Sertoli cells can progress through discrete steps in the sequence of spermatogenesis during short-term culture, including initiation or completion of meiosis and initiation of spermiogenesis (Rassoulzadegan et al., "Transmeiotic Differentiation of Male Germ Cells in Culture," *Cell* 75: 997–1006 (1993); Hue et al., "Meiotic Differentiation of Germinal Cells in Three-Week Cultures of Whole Cell Population from Rat Seminiferous Tubules," *Biol. Reprod.* 59:379–387 (1998); Hofmann et al., "Immortalized Germ Cells Undergo Meiosis In vitro," *Proc. Natl.*

Acad. Sci. USA 91:5533–5537 (1994); and Tesarik et al., "In-vitro Differentiation of Germ Cells from Frozen Testicular Biopsy Specimens," Hum. Reprod. 15:1713–1716 (2000)). However, long-term culture conditions that result in the progression of undifferentiated mammalian gonocytes through spermatocytogenesis and meiosis have not been reported.

The complex Sertoli-germ cell interactions required for the orchestration of spermatogenesis in vivo (Griswold, "The Central Role of Sertoli Cells in Spermatogenesis," Semin. Cell Dev. Biol. 9:411–416 (1998)), including intercellular junctions and endocrine and paracrine regulation, appear to be critical to the in vitro process also, as culture systems utilizing tubule fragments (Hue et al., "Meiotic Differentiation of Germinal Cells in Three-Week Cultures of Whole Cell Population from Rat Seminiferous Tubules," Biol. Reprod. 59:379–387 (1998)) or homogenates (Tesarik et al., "In-vitro Differentiation of Germ Cells from Frozen Testicular Biopsy Specimens," Hum. Reprod. 15:1713–1716 (2000)) stimulate germ cell differentiation more successfully than other approaches. A potential limitation to this approach is the permeability barrier to critical medium constituents created by peritubular cells and basement membrane components that persist in tubule fragments. To avoid this potential constraint, peritubular cells can be removed and seminiferous tubules were completely dissociated enzymatically (Karl et al., "Sertoli Cells of the Testis: Preparation of Cell Cultures and Effects of Retinoids," Methods Enzymol. 190:71–75 (1990)). Direct association among testis cells (germ cells and Sertoli cells) can be reestablished by aggregation with lectins such as concanavalin A (Grootegoed et al., "Concanavalin A-Induced Attachment of Spermatogenic Cells to Sertoli Cells In vitro," Exp. Cell Res. 139:472–475 (1982)).

The present invention is directed to overcoming these and other deficiencies in the art.

SUMMARY OF THE INVENTION

The present invention relates to a method of in vitro spermatogenesis.

This method involves isolating a plurality of Sertoli cells and a plurality of undifferentiated diploid germ cells from a testis of a male mammal. The Sertoli cells and germ cells are aggregated to yield Sertoli-germ cell aggregates. The Sertoli-germ cell aggregates are encapsulated to yield a plurality of tubule-like structures containing both Sertoli cells and germ cells. The tubule-like structures are then transferred to a culture medium. The tubule-like structures are then cultured under conditions effective to allow the Sertoli cells and the germ cells to interact, allowing the germ cells to progress through spermatocytogenesis and meiosis to produce a plurality of differentiated haploid spermatids. The present invention also relates to round spermatids produced by the method described above, where the round spermatids are haploid.

The present invention also relates to a method of overcoming male infertility in mammals. This method involves providing a haploid round spermatid of a male mammal produced through in vitro spermatogenesis. The round spermatid or a portion of the round spermatid is introduced into an oocyte of a female mammal of the same species as the male mammal under conditions effective to produce a fertilized egg.

In one embodiment of the method of overcoming male infertility in mammals, the portion of the round spermatid introduced into the female mammal's oocyte is the nucleus of the round spermatid.

The present invention also relates to an isolated haploid spermatid.

The in vitro spermatogenesis method of the present invention is useful in studying the in vivo spermatogenesis process. The in vitro spermatogenesis method of the present invention is also useful for developing an effective IVS procedure to generate developmentally competent haploid spermatids or sperm to be used in conjunction with various in vitro fertilization techniques useful for treating or overcoming male factor infertility, including, without limitation, such techniques as the ICSI or ROSI procedures in treating selected causes of male infertility (Palermo et al., "Pregnancies After Intracytoplasmic Sperm Injection of Single Spermatozoon into an Oocyte," Lancet 340:17–18 (1992); Van Steirteghem et al., "Use of Assisted Fertilization," Hum. Reprod. 8:1784–1785 (1993); and Tesarik et al., "Restoration of Fertility by In-vitro Spermatogenesis," Lancet 353:555–556 (1999), which are hereby incorporated by reference in their entirety).

The in vitro spermatogenesis method of the present invention is also effective in improving long-term culture conditions such that germ cell differentiation can be achieved when starting with an infantile testis. This aspect of the present invention provides an enhanced approach to treating male factor infertility, and makes feasible the option of preserving testicular tissue for future use from young males mammals expected to lose gonadal function due to chemotherapy or other treatments.

The present invention also involves the use of the round spermatids produced from the in vitro spermatogenesis method described herein for use in applications of procedures involving genetic modification of the germ line of domestic and laboratory animals and conservation efforts for threatened and endangered species where male fertility is an issue. The present invention further involves the use of the round spermatids produced from the in vitro spermatogenesis method (as described herein) for use in conserving the male germ plasm of commercially valuable domestic, companion, or exotic species.

BRIEF DESCRIPTION OF THE DRAWINGS

FIGS. 1A–D are micrographs of neonatal bull testicular cells before and after culture in vitro.

FIG. 2A illustrates the expression pattern of protamine-2 (PRM-2) (140 bp), transition protein-1 (TP-1) (150 bp), and GAPDH (379 bp) genes in testis from a neonatal bull following culture in vitro based on RT-PCR. The detection of mRNA in the same sample by Northern blot analysis is shown for: protamine-2 (0.47 Kb) in FIG. 2B, transition protein-1 (0.37 Kb) in FIG. 2C, and GAPDH in FIG. 2D. Lanes: M, MW marker (50 bp ladder); 1, 3 day-old testis; 2, 2-week culture; 3, 5-week culture; 4, 10-week culture; 5, adult testis; 6, negative control.

DETAILED DESCRIPTION OF THE INVENTION

The present invention relates to a method of in vitro spermatogenesis for mammals. This method involves the use of Sertoli cells and undifferentiated diploid germ cells isolated from a male mammal to produce haploid spermatids. The haploid spermatids can then be used in various processes to facilitate the study of spermatogenesis, to treat male factor infertility, and to genetically modify the male germ line of mammals.

Definitions of certain terms that are relevant to the present invention, as used herein, are included below:

The term "germ cell" refers to cells in the testis derived from primordial germ cells. These cells are also referred to herein as "spermatogenic" cells.

The term "gonocyte" refers to the type of germ cell present in the neonatal testis. Gonocytes have 2C DNA (diploid) and are precursors to spermatogonia.

The term "spermatid" generally refers to a haploid (1C) cell that is produced by meiotic division of secondary spermatocytes. These cells develop into sperm without dividing. Spermatids upon initial formation are characteristically round and unflagellated.

The term "spermatozoon" refers to the mature, male reproductive cell (i.e., gamete, sperm cell) of mammals.

The term "spermatogonia" refers to pre-meiotic stem cells to the process of spermatogenesis.

The term "spermatogonial stem cell" refers to the type of spermatogonia that are true stem cells, resistant to environmental insult, and renew the spermatogonia population throughout adult life.

The term "spermatocyte" refers to the cell types which develop after spermatogonia but before spermatids.

The term "primary spermatocyte" means a tetraploid (4C) cell which develops from Type B (secondary) spermatogonia and carries out the processes of meiotic prophase.

The term "secondary spermatocyte" refers to haploid but 2C cells produced by meiotic division of primary spermatocytes.

The term "mature spermatid" refers to a spermatid with mitochondria fully helical, chromatin fully condensed, cytoplasm shed; appears like sperm, but mature spermatid is still attached to Sertoli cell The term "Sertoli cell" refers to a type of cell located in the testes of mammals. These cells typically line the tubules of the testes and nurture the developing sperm cells. Sertoli cells provide support for germ cells. They also are believed to provide an environment for germ cells to develop and mature and substances initiating meiosis of the diploid germ cells. Further, Sertoli cells create a barrier in which the seminiferous tubules of the male testis is divided into two environments for the development of spermatozoa.

The term "spermatogenesis" refers to the process by which undifferentiated diploid male germ cells develop into differentiated haploid sperm cells. In mammals, spermatogenesis involves three major phases, which occur in sequence: (1) the Mitosis Phase; (2) the Meiosis Phase; and (3) the Spermiogenesis Phase. During the Mitosis Phase, spermatogonia undergo mitosis, thereby resulting in a proliferation of diploid spermatogonia. In this phase, the spermatogonia divide four to six times to produce a pool of spermatogonia which are committed to develop into mature sperm cells. The spermatogonia also renew themselves. The Meiosis Phase involves the reduction of the chromosome number of the germ cells from diploid to haploid. This phase generally begins with the diploid spermatogonia (2C DNA) undergoing the S phase of meiosis I to become primary spermatocytes (having 4C DNA). These primary spermatocytes carry out the unique functions of chromosome pairing and DNA recombination. The Meiosis Phase ends with two meiotic cell divisions. The first division separates homologous chromosomes and produces secondary spermatocytes. In the second division, the secondary spermatocytes each produce two haploid round spermatids (1C DNA). During the Spermiogenesis Phase, the round spermatids develop into mature, differentiated sperm cells. The round spermatids, without further division, develop into sperm by forming an acrosome and flagellum, shedding excess cytoplasm, and condensing and shaping the nucleus in a species-specific manner. Thus, the Spermiogenesis Phase prepares the sperm cells to have the motility and interaction functions needed to fertilize the egg of the counterpart female mammal.

As used herein, the term "in vitro spermatogenesis" generally refers to the process by which undifferentiated diploid male germ cells develop into differentiated haploid spermatids. This involves the first two phases, the Mitosis Phase and the Meiosis Phase, of spermatogenesis (as described above).

In one embodiment, the in vitro spermatogenesis method of the present invention involves isolating a plurality of Sertoli cells and a plurality of undifferentiated diploid germ cells from a testis of a male mammal. The Sertoli cells and germ cells are aggregated to yield Sertoli-germ cell aggregates. The Sertoli-germ cell aggregates are encapsulated to yield a plurality of tubule-like structures containing both Sertoli cells and germ cells. The tubule-like structures are transferred to a culture medium. The tubule-like structures are then cultured under conditions effective to allow the Sertoli cells and the germ cells to interact, allowing the germ cells to progress through spermatocytogenesis and meiosis to produce a plurality of differentiated haploid spermatids. Suitable undifferentiated diploid germ cells for use in the in vitro spermatogenesis method of the present invention include, for example, gonocytes.

Suitable sources of the Sertoli cells and germ cells are the testes of various mammals, including, without limitation, humans, bovines, porcines, and rodents. In one aspect of the present invention, the source of Sertoli cells and germ cells is testicular tissue taken from a portion of a testis of a mammal. The Sertoli cells and germ cells may be taken from fresh or stored testes or testicular tissue. In the case of stored testes, the testes may be stored in a frozen state under conditions to preserve the Sertoli cells and germ cells for use in the in vitro spermatogenesis method of the present invention. The storage of the testes may be long-term or short-term. In one embodiment, the testes are stored using cryopreservation techniques known in the art; for example, by using liquid nitrogen or by freeze-drying. Cryopreserved testes may be thawed prior to use in the in vitro spermatogenesis method of the present invention, and in accordance with known freeze-thaw procedures for mammalian tissue.

Suitable testes or testicular tissue used as sources of Sertoli cells and germ cells may be taken from mammals of all ages, i.e., ranging in age from neonatal to adult. In one embodiment, the mammal is a neonatal male. As used herein, the term "neonatal male" refers to a newborn male. In a preferred embodiment, the neonatal male ranges in age from 1 to 5 days old. In another embodiment, the mammal is a pre-pubertal male. As used herein, a "pre-pubertal male" is a male that has passed the neonatal stage, but that has not yet entered the peri-pubertal stage (i.e., near or around pubertal age). In yet another embodiment, the mammal is a peri-pubertal male. As used herein, a "peri-pubertal male" is a male that has passed the pre-pubertal stage and is near or around the age of puberty. In another embodiment, the mammal is a male in the puberty stage. In yet another embodiment, the mammal is a juvenile male. As used herein, the term "juvenile male" refers to a youthful male that has passed the age of puberty but that has not yet matured into an adult. In still another embodiment, the mammal is an adult male. As used herein, an "adult male" is a mature male that has passed juvenile stage. The ages encompassing each of the above-referenced male age groups (i.e., neonatal, pre-pubertal, peri-pubertal, puberty, juvenile, and adult) varies from species to species, and is interpreted herein to correspond to the ages recognized in the art with respect to each mammalian species.

In one embodiment of the in vitro spermatogenesis method of the present invention, the Sertoli cells and the undifferentiated diploid germ cells are isolated from a testis of a male mammal by decapsulation of the testis to expose seminiferous tubules containing Sertoli cells and undifferentiated germ cells. The Sertoli cells and undifferentiated germ cells are dissociated from the seminiferous tubules using dissociating techniques known in the art. The Sertoli cells and undifferentiated germ cells are then segregated from the other testicular components (e.g., the peritubular cells).

In a preferred embodiment, the in vitro spermatogenesis method of the present invention involves decapsulating a portion of the testis to yield exposed parenchyma tissue containing a plurality of seminiferous tubules containing Sertoli cells and germ cells. The Sertoli and germ cells are dissociated from the seminiferous tubules using a first enzyme solution to yield a mixture including peritubular cells, dissociated Sertoli cells, dissociated germ cells, and dissociated seminiferous tubules. The dissociated Sertoli cells, germ cells, and seminiferous tubules are separated from the peritubular cells. Then, the dissociated Sertoli cells, germ cells, and seminiferous tubules are incubated in a second enzyme solution which assists in releasing the dissociated Sertoli and germ cells from the seminiferous tubules.

Suitable methods for decapsulation of the testis involves the use of manual decapsulation techniques known in the art. In a preferred embodiment, manual decapsulation involves removal of the tunica albuginea of the testis under conditions effective to expose the parenchyma tissue of the subject testis. The exposed parenchyma tissue can then be prepared for isolation of the Sertoli cells and germ cells. As an example, the parenchyma tissue may be cut into sections in order to create more surface area and then washed in a phosphate buffered saline solution. A suitable saline solution includes $Ca^{++}$, $Mg^{++}$-free phosphate buffered saline (PBS).

Thereafter, the washed parenchyma tissue may be exposed to an enzyme solution suitable to dissociate the Sertoli cells and germ cells from the seminiferous tubule fragments. Suitable enzyme solutions for this purpose are those having the ability to yield a mixture of peritubular cells, dissociated Sertoli cells, dissociated germ cells, and dissociated seminiferous tubules, or fragments of tubules. An example of a suitable enzyme solution for this purpose is a solution containing collagenase, DNase I, trypsin inhibitor, and hyaluronidase. More specifically, for a parenchyma sample size of about 2 grams, a suitable enzyme solutions would measure about 50 mL, and contain approximately 0.5 mg/mL collagenase, 10 μg/mL DNase I, 1.0 μg/mL soybean trypsin inhibitor, and 1.0 μg/mL hyaluronidase in $Ca^{++}$, $Mg^{++}$-free PBS. In a preferred embodiment, incubation of the parenchyma tissue is for a period of about 30 minutes at ambient temperature (e.g., approximately 25° C.).

After dissociation, the mixture of dissociated cells and tubule fragments may then be manipulated in order to separate the Sertoli cells and germ cells from the peritubular cells and tubule fragments. In one embodiment, this separation is achieved using centrifugation techniques well known in the art. In a preferred embodiment, the mixture of cells and tubule fragments are centrifuged at approximately 400×g to allow the removal of the peritubular cells. The remaining pellet is then incubated for approximately 30 minutes with the enzyme solution described above, except that the amount of collagenase is increased to approximately 5 mg/mL. The mixture is then centrifuged again at approximately 600×g for about 10 minutes, and the supernatant discarded, resulting in a remaining pellet containing the dissociated Sertoli cells and germ cells.

Once the dissociated Sertoli cells and germ cells are isolated from the parenchyma tissue, they may be processed for storage (i.e., long-term or short-term storage) or reaggregated for use in producing haploid round spermatids, which in turn may be used in various in vitro fertilization methods or to further develop into mature sperm cells. In one embodiment, dissociated Sertoli cells and germ cells are washed in Dulbecco modified Eagle medium/F12 (DMEM/F12) medium (Gibco) and, thereafter, placed immediately into culture or frozen and stored in liquid nitrogen.

A suitable method for freezing the testicular cells (i.e., the Sertoli cells and undifferentiated germ cells) involves suspending the cells in DMEM/F12 at a concentration of approximately $1 \times 10^9$ cells/mL. A suitable freezing medium is then added and then the mixture is stored at a suitable low temperature. In a preferred embodiment, the freezing medium contains approximately 10 percent dimethyl sulfoxide and 20 percent bovine calf serum (BCS) in DMEM/F12. The freezing medium is slowly added to the mixture of cells up to a volume equal to that of the original cell suspension, and then mixed. A suitable low temperature includes temperatures of at least as low as −60° C., and preferably as low as at least −70° C. In a preferred embodiment, this is achieved by incubating aliquots of the final cell suspension (for example, 1.0 mL per cryovial) at −70° C. for at least 12 hours, and then storing the aliquots in liquid $N_2$.

Frozen aliquots of the isolated Sertoli cells and germs cells may then be thawed and reaggregated. In one embodiment, the frozen Sertoli cells and germ cells are thawed in a temperature of between about 25–36° C., and preferably at about 32° C. In a preferred embodiment, the cryovials containing the frozen testicular cells are swirled in a 32° C. water bath, with the addition of DMEM/F12 to five times the initial volume (Dobrinski et al., "Transplantation of Germ Cells from Rabbits and Dogs into Mouse Testes," Biol. Reprod. 61:1331–1339 (1999), which is hereby incorporated by reference in its entirety). Thereafter, the thawed cell suspension is centrifuged to concentrate the testicular cells in a pellet, which may then be resuspended DMEM/

F12 for reaggregation. Suitable centrifugation conditions include centrifugation at approximately 600×g for between about 8–12 minutes.

The present invention also relates to the aggregation of the isolated Sertoli and germ cells and the encapsulation of these reaggregated testicular cells. In one embodiment, the reaggregation is carried out using a chemical aggregating agent. An example of a suitable chemical aggregating agent is phytohemagglutinin. A preferred embodiment involves washing the dissociated cells from fresh testis or from frozen-thawed cell suspensions (as described herein above) and resuspending the cells to approximately $1\times10^9$ cells/mL in DMEM/F12 medium containing about 0.5 percent BCS (Hyclone, Logan, Utah) and in about 100 µg/ml phytohemagglutinin (Sigma). The resuspension is incubated under conditions effective to yield reaggregated Sertoli cells and germ cells. In a preferred embodiment, the resuspened cells are incubated for approximately 10 minutes at about 32° C. in the resuspension medium.

The present invention also involves the encapsulation of the Sertoli-germ cell aggregates. In one embodiment, this is carried out by using a chemical encapsulating agent. A suitable chemical encapsulating agent includes, without limitation, sodium alginate. For example, after incubation, the reaggregated cells are collected using suitable separation techniques, including, without limitation, centrifugation techniques well known in the art. The isolated reaggregated Sertoli cells and germ cells are then incubated with sodium alginate (Sigma) in NaCl under conditions effective to prevent disruption of the pellet. In a preferred embodiment, the sodium alginate solution contains approximately 1.0 percent sodium alginate in 0.9 percent NaCl, and the cells are incubated in this solution for approximately 8–12 minutes at between about 28–34° C. The aggregated, alginate-treated cells may then be extruded into a sodium alginate solution in a Petri dish using a fire-polished Pasteur pipette (e.g., 200 µm outside diameter (o.d.)). The extruded strands of alginate-treated cells is then drawn with a column of approximately 1.0 percent sodium alginate into the tip of a Pasteur pipette (e.g., 1.0 mm o.d.) and solidified by transferring into a suitable amount of $CaCl_2$ (e.g., 1.5 percent) in NaCl (e.g., 0.9 percent). The alginate-encapsulated cells, which include tubule-like structures, may then be transferred to a suitable culture medium for use in the culturing of haploid round spermatids.

The culture medium for use in the present invention should be effective to stimulate Sertoli cell function and consequently germ cell proliferation and differentiation to haploid round spermatids. A suitable culture medium that may be used for culturing the tubule-like structures produced during the in vitro spermatogenesis method of the present invention may include, without limitation, HEPES-buffered DMEM/F12 medium supplemented with insulin-transferrin-selenium solution, vitamin C, vitamin E, retinoic acid, retinol, pyruvate, bovine FSH, testosterone, antibiotic-antimycotic solution, and BCS. In one aspect of the present invention, the culturing of the tubule-like structures may be carried out in the culture medium for up to 20 weeks, at a temperature in a humidified atmosphere of about 5 percent carbon dioxide in air. Preferably, the culturing may be carried out in the culture medium for a period of 2, 5, 10, or 14 weeks.

In a preferred embodiment, the culture medium may contain modified HEPES-buffered DMEM/F12 medium supplemented with approximately 10 µg/mL insulin-transferrin-selenium solution (Gibco), approximately $10^{-4}$ M vitamin C (Sigma), approximately 10 µg/ml vitamin E (Sigma), approximately $3.3\times10^{-7}$ M retinoic acid (Sigma), approximately $3.3\times10^{-7}$ M retinol (Sigma), approximately 1 mM pyruvate (Sigma), approximately $2.5\times10^{-5}$ U bovine FSH (SIOUX, Sioux Center, Iowa), approximately $10^{-7}$ M testosterone (Sigma), approximately 1× antibiotic-antimycotic solution (Gibco), and approximately 10% BCS (Weiss et al., "Pre- and Postmeiotic Expression of Male Germ Cell-Specific Genes Throughout 2-Week Cocultures of Rat Germinal and Sertoli Cells," Biol. Reprod. 57: 68–76 (1997), which is hereby incorporated by reference in its entirety). The alginate-encapsulated cell aggregates can be transferred to approximately 1.0 mL of culture medium in a 24-well dish (Falcon, Becton-Dickinson, Lincoln Park, N.J.) and cultured for up to 14 weeks at approximately 32° C. in a humidified atmosphere of 5 percent $CO_2$ in air. Further, approximately 80 percent of culture medium is replaced on alternate days.

The present invention also relates to the haploid round spermatids produced by the in vitro spermatogenesis method of the present invention, as described herein.

The present invention also relates to an isolated haploid spermatid. In one embodiment, the isolated haploid spermatid is isolated from a male mammal. Suitable male mammals for use in the isolation of haploid spermatids include, without limitation, humans, bovines, porcines, and rodents.

The present invention also relates to an isolated haploid spermatid that is derived from an undifferentiated diploid germ cell. In one embodiment, the undifferentiated diploid germ cell is a gonocyte. Suitable sources for the undifferentiated diploid germ cell include male mammals of any age (i.e., ranging in age from neonatal males to adult males of a given species of mammal). In one embodiment, the male mammal is a human, a bovine, a porcine, or a rodent. In another embodiment, the male mammal is a neonatal male, a juvenile male, a peri-pubertal male, or an adult male. In a preferred embodiment, the male mammal is a neonatal bovine male ranging in age from 1 to 5 days old. In yet another preferred embodiment, the male mammal is a neonatal bovine male of 3 days old, a peri-pubertal bovine male, or an adult bovine male.

The present invention also relates to a method of overcoming male infertility in mammals involving (1) providing a haploid round spermatid of a male mammal produced through in vitro spermatogenesis and (2) introducing the round spermatid or a portion of the round spermatid into an oocyte of a female mammal of the same species as the male mammal under conditions effective to produce a fertilized egg.

In one embodiment of the present invention, round spermatids or portions thereof are introduced into the oocyte using microinjection (Palermo et al., "Pregnancies After Intracytoplasmic Sperm Injection of Single Spermatozoon into an Oocyte," Lancet 340:17–18 (1992); Van Steirteghem et al., "Use of Assisted Fertilization," Hum. Reprod. 8:1784–1785 (1993); Tesarik et al., "Treatments of Severe Male Infertility By Micromanipulation-Assisted Fertilization: News and Views," Frontiers In Bioscience 3:e238–246 (1998); Staub, "A Century of Research On Mammalian Male Germ Cell Meiotic Differentiation In Vitro," J. Andrology 22(6):911–926 (2001); and Tesarik et al., "Restoration of Fertility by In-vitro Spermatogenesis," Lancet 353: 555–556 (1999), which are hereby incorporated by reference in their entirety). In another embodiment, introduction of the round spermatids or portions thereof into the oocyte is by intracytoplasmic sperm injection (Palermo et al., "Pregnancies After Intracytoplasmic Sperm Injection of Single Spermatozoon into an Oocyte," *Lancet* 340:17–18 (1992); Van Steirteghem et al., "Use of Assisted Fertilization," *Hum. Reprod.* 8:1784–1785 (1993); and Tesarik et al., "Restoration of Fertility by In-vitro Spermatogenesis," *Lancet* 353: 555–556 (1999), which are hereby incorporated by reference in their entirety). Alternatively, round spermatid injection techniques and/or round spermatid nuclear injection techniques may be used in combination with intracytoplasmic sperm injection (Palermo et al., "Pregnancies After Intracytoplasmic Sperm Injection of Single Spermatozoon into an Oocyte," *Lancet* 340:17–18 (1992); Van Steirteghem et al., "Use of Assisted Fertilization," *Hum. Reprod.* 8:1784–1785 (1993); Tesarik et al., "Restoration of Fertility by In-vitro Spermatogenesis," *Lancet* 353: 555–556 (1999); Tesarik et al., "Viable Embryos From Injection of Round Spermatids Into Oocytes," *N. Engl. J. Med.* 333 (8):525 (1995); Tesarik et al., "Spermatid Injection Into Human Oocytes. II. Clinical Application in the Treatment of Infertility Due to Non-Obstructive Azoospermiam," *Hum. Reprod.* 11:780–783 (1996); Tesarik et al., "Spermatid Injection Into Human Oocytes. I. Laboratory Techniques and Special Features of Zygote Development," *Hum. Reprod.* 11:772–779 (1996); Vanderzwalmen et al., "Intracytoplasmic Injection of Spermatids Retrieved From Testicular Tissue: Influence of Testicular Pathology, Type of Selected Spermatids and Oocyte Activation," *Hum. Reprod.* 12:1203–1213 (1997); and Barak et al., "Pregnancy and Birth After Transfer of Embryos That Developed From Single-Nucleated Zygotes Obtained By Injection of Round Spermatids Into Oocytes," *Fertil. Steril.* 70:67–70 (1998), which are hereby incorporated by reference in their entirety).

EXAMPLES

Example 1

In vitro Production of Haploid Germ Cells from Fresh or Frozen-thawed Testicular Cells of Neonatal Bulls The objective of this study was to develop a procedure for achieving male germ cell progression through meiosis in vitro. Testes from 3-day-old bulls were decapsulated and seminiferous tubules were dissociated enzymatically to recover Sertoli and germ cells. Dissociated cells were reaggregated by phytohemagglutinin and encapsulated by calcium alginate, then cultured for up to 14 weeks in modified Dulbecco modified Eagle medium/F12 (DMEM/F12) medium (32° C., 5% $CO_2$ in air). At 2, 5, and 10 weeks, cultured cells were examined and evaluated by reverse transcription-polymerase chain reaction (RT-PCR) and Northern blot analysis for protamine-2 (PRM-2) and transition protein-1 (TP-1) mRNA, expressed specifically in round spermatids. Ploidy was characterized by flow cytometric analysis of DNA content of cultured cells. Only Sertoli cells and gonocytes were observed in seminiferous tubules of 3-day-old testes. By 10 weeks of culture, small spherical cells (7–10 µm) were apparent at the margin of cell associations in culture. Following RT-PCR and Northern blot analysis, specific bands corresponding to PRM-2 and TP-1 were detected only in adult testis RNA or after 10 weeks of culture. Based on flow cytometry, a haploid population of cells appeared in vitro which was not in 3-day-old bull testis. The novel culture system developed in this study is the first to promote differentiation of gonocytes to presumptive spermatids in vitro based on the expression of spermatid-specific genes.

The primary objective of this study was to determine if dissociated cells of the neonatal bovine testis, both fresh and frozen-thawed, could be reassembled to recapitulate spermatogenesis during long-term culture. Testis cells from dissociated seminiferous tubules were reaggregated and encapsulated in calcium alginate to promote and sustain interaction between germ cells and Sertoli cells without limiting permeability to media components. Results indicate that these conditions promoted germ cell differentiation from gonocytes to presumptive round spermatids.

Example 2

Testis Dissociation

The tunica albuginea was manually decapsulated from 3-day-old bull testes, and 2 g of the exposed parenchyma were cut into pieces and washed for 20 minutes in $Ca^{++}$, $Mg^{++}$-free phosphate buffered saline (PBS) (Sigma Chemical Co, St. Louis, Mo.). Tissue was dissociated in 50 ml of enzyme solution A containing 0.5 mg/ml collagenase (Type A ,Sigma), 10 µg/ml DNase I (Sigma), 1 µg/ml soybean trypsin inhibitor (Gibco BRL, Grand Island, N.Y.), and 1 mg/ml hyaluronidase (Sigma) in $Ca^{++}$, $Mg^{++}$-free PBS, and incubated for 30 minutes at ambient temperature (~25° C.). Dissociated cells and tubule fragments were centrifuged at 400×g and decanted to remove peritubular cells, then the material was incubated with enzyme solution B (same as solution A with collagenase increased to 5 mg/ml) for 30 minutes. The material was centrifuged at 600×g for 10 minutes.

After centrifugation, the supernatant was removed and dissociated cells were washed twice in Dulbecco modified Eagle medium/F12 (DMEM/F12) medium (Gibco), then placed immediately into culture or frozen and stored in liquid nitrogen. For freezing, testicular cells were suspended in DMEM/F12 at a concentration of $1 \times 10^9$ cells/ml. Freezing medium (10% dimethyl sulfoxide, 20% bovine calf serum (BCS) in DMEM/F12) was added slowly to a volume equal to the original cell suspension, and mixed. Aliquots of the final cell suspension (1.0 ml per cryovial) were held at −70° C. for at least 12 hours, and then stored in liquid $N_2$. Swirling in a 32° C. water bath thawed cells, and DMEM/F12 was added slowly to five times the initial volume (Dobrinski et al., "Transplantation of Germ Cells from Rabbits and Dogs into Mouse Testes," *Biol. Reprod.* 61:1331–1339 (1999), which is hereby incorporated by reference in its entirety). The thawed cell suspension was centrifuged at 600×g for 10 minutes, and the cell pellet was resuspended in DMEM/F12 for reaggregation.

Example 3

Calcium Alginate Encapsulation and in vitro Culture

Washed, dissociated cells from fresh testis or frozen-thawed cell suspensions were resuspended to $1 \times 10^9$ cells/ml in DMEM/F12 medium containing 0.5% BCS (Hyclone, Logan, Utah) and $1 \times 10^9$ g/ml phytohemagglutinin (Sigma). After incubation for 10 minutes at 32° C., reaggregated cells were centrifuged, the supernatant was removed, and 1.0% sodium alginate (Sigma) in 0.9% NaCl was added without disrupting the pellet. After further incubation for 10 minutes at 32° C., the aggregated, alginate-treated cells were extruded into 1.0 ml sodium alginate solution in a Petri dish using a fire-polished Pasteur pipette (200 µm outside diameter (o.d.)). Extruded strands of alginate-treated cells were drawn with a column of 1.0% sodium alginate into the tip of a 9" Pasteur pipette (1.0 mm o.d.) and solidified by transferring into 1.5% $CaCl_2$ in 0.9% NaCl. Alginate-encapsulated cells were then transferred to culture medium.

Culture medium consisted of modified HEPES-buffered DMEM/F12 medium supplemented with 10 g/ml insulin-transferrin-selenium solution (Gibco), $10^{-4}$ M vitamin C (Sigma), 10 µg/ml vitamin E (Sigma), $3.3\times10^{-7}$ M retinoic acid (Sigma), $3.3\times10^{-7}$ M retinol (Sigma), 1 mM pyruvate (Sigma), $2.5\times10^{-5}$ U bovine FSH (SIOUX, Sioux Center, Iowa), $10^{-7}$ M testosterone (Sigma), 1× antibiotic-antimycotic solution (Gibco), 10% BCS (Weiss et al., "Pre- and Postmeiotic Expression of Male Germ Cell-Specific Genes Throughout 2-Week Cocultures of Rat Germinal and Sertoli Cells," Biol. Reprod. 57: 68–76 (1997), which is hereby incorporated by reference in its entirety). Alginate-encapsulated cell aggregates were transferred to 1.0 ml of culture medium in a 24-well dish (Falcon, Becton-Dickinson, Lincoln Park, N.J.) and cultured for up to 14 weeks at 32° C. in a humidified atmosphere of 5% $CO_2$ in air. Approximately 80% of culture medium was replaced on alternate days. The cell culture protocol was repeated on three separate cell preparations from two bulls.

Example 4

Histological Examination

Tissue from 3-day-old bull testis was fixed in Bouin fluid, embedded in paraffin wax, and sectioned at 5 µm using standard histological procedures for examination of starting material. Sections were then stained with hematoxylin and eosin. Cultured, encapsulated cells were recovered and examined before and after dissociation using an Olympus inverted microscope with phase-contrast and Hoffman illumination.

Example 5

RNA Preparation and Analysis Using Reverse Transcription-polymerase Chain Reaction (RT-PCR) and Northern Blot Analysis The mRNA expression of protamine-2 (PRM-2) and transition protein-1 (TP-1) was assessed in cultured cells from neonatal bull testes using RT-PCR and Northern blot analysis. At 0 (3-day-old testis), 2, 5, and 10 weeks of culture, total RNA of cultured cells was extracted by the Trizol method (Gibco).

Reverse transcription was carried out using 200 ng of total RNA, 5 mM $MgCl_2$, 1 U of RNase inhibitor, and 0.2 U of DNase I at 37° C. for 30 minutes, then 42° C. for 1 hour after adding 1 mM dNTP, 2.5 µM random hexamers, and 2.5 U murine leukemia virus (MuLV) reverse transcriptase (Roche, Branchburg, N.J.) (Huang et al., "Optimization of DNase I Removal of Contaminating DNA from RNA for Use in Quantitative RNA-PCR," Biotechniques 20:1012–1020 (1996), which is hereby incorporated by reference in its entirety). The PCR for PRM-2 (5'-aga ggc cgc tac cac tac aga cac a-3' (SEQ ID NO:1), 5'-act tag agc tgc ctt ccg cat ctc c-3' (SEQ ID NO:2); 140 bp) (Kremling et al., "The Bovine Protamine 2 Gene: Evidence for Alternative Splicing," Biochim. Biophys. Acta 1132:133–139 (1992), which is hereby incorporated by reference in its entirety), TP-1 (5'-gga aga gca gcc tga aga gt-3' (SEQ ID NO:3), 5'-tca ggt ctc ctt ggc agt cc-3' (SEQ ID NO:4), 150 bp) (Kim et al., "Nucleotide Sequence and Exon-Intron Structure of the Bovine Transition Protein 1 Gene," DNA Seq. 3:123–125 (1992), which is hereby incorporated by reference in its entirety) and glyceraldehyde 3-phosphate dehydrogenase (GAPDH, 5'-acg gca cag tca agg cag ag-3' (SEQ ID NO:5), 5'-gtg atg gcg tgg aca gtg gt-3' (SEQ ID NO:6); 379 bp, from GenBank U85042) was performed in a 20 µl reaction containing 10 mM Tris-HCl (pH 8.3), 2 mM $MgCl_2$, 50 mM KCl, 0.25 mM dNTP, 3–5 pmol of each primer, and 1.25 U of Taq DNA polymerase (Gibco). The PCR was initiated with denaturation at 94° C. for 5 minutes followed by 40 cycles of 30 sec at 94° C., 30 sec at 65° C., and 30 sec at 72° C. A final extension for 10 minutes at 72° C. completed the PCR; then PCR products were separated by 2% agarose gel electrophoresis and verified by automated nucleotide sequencing. Negative controls included mock reverse transcription without RNA or PCR with distilled deionized water. Testicular cells from adult testis were used as positive control.

Northern blot analysis was by the protocol of Wang and Johnson (Wang et al., "Complementary Deoxynucleic Acid Cloning and Sequence Analysis of the Alpha-Subunit of Inhibin from Chickenovarian Granulose Cells," Biol. Reprod. 49:453–458 (1993), which is hereby incorporated by reference in its entirety). Briefly, 15 µg of total RNA per sample was electrophoresed in a denaturing 1.5% agarose, 2.2 M formaldehyde gels in 1× morpholinepropanesulfonic acid (MOPS). Gels were blotted onto nitrocellulose membrane (Genescreen Plus) (New England Nuclear, Boston, Mass.). $^{32}$P-Labeled probes were prepared using random labeling kit (Stratagene, La Jolla, Calif.). Hybridization was performed at 42° C. in a solution of 1% sodium dodecyl sulfate (SDS) (Gibco), 50% formamide (Sigma), 2 mg/ml herring sperm DNA (Gibco), 5× Denhardt's reagent, and 5×SSPE (1×SSPE is 0.18 M NaCl, 10 mM $NaPO_4$, and 1 mM EDTA (pH 7.7)). Following hybridization, the membrane was washed at a final stringency of 65° C. in 0.1× saline-sodium citrate (SSC) (0.15 M NaCl and 0.015 M sodium citrate) and exposed for appropriate times using Kodak X-OMAT autoradiographic film.

Example 6

Flow Cytometric Analysis of DNA Content

Flow cytometry was carried out to differentiate germ cell populations based on nuclear DNA content. Encapsulated cells were isolated mechanically after 10- and 14-weeks of culture, washed in $Ca^{++}$, $Mg^{++}$-free PBS, and permeabilized with 0.1% triton-X (Sigma) for 30 minutes. Testicular cells from adult and 3 day-old bulls were prepared as controls with and without haploid germ cells, respectively. Cell nuclei were stained with propidium iodide (Sigma) at 50 µg/ml, and single color analysis for DNA ploidy was completed on $2\times10^4$ cells/sample using a Becton Dickinson FACS Calibur flow cytometer.

Example 7

Figure 1:
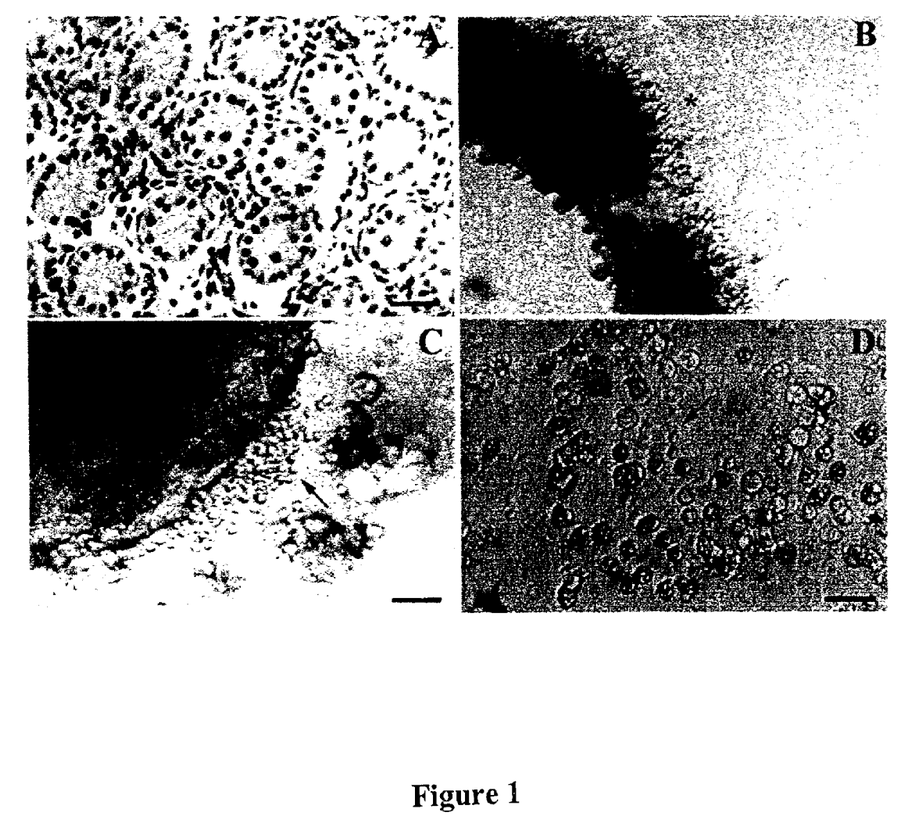
FIG. 1A shows Sertoli cells and gonocytes within the seminiferous tubule of a 3-day-old bull testis. Bar=50 $\mu$m.
FIG. 1B shows calcium alginate (*) encapsulated testicular cells.
FIG. 1C shows small spherical cells (7–10 $\mu$m) appearing at 10 weeks of culture. Bar=50 $\mu$m.
FIG. 1D shows a cell suspension after disaggregation of alginate-encapsulated cells at 10 weeks of culture (arrow—presumptive round spermatid). Bar=20 $\mu$m.

Morphological and Histological Analysis of Encapsulated Cells Cultured in vitro from Fresh and Frozen-thawed Testicular Cells of 3-Day-old Bulls Parenchyma of 3-day-old bull testis was characterized by seminiferous tubules containing only immature Sertoli cells and gonocytes (FIG. 1A). The integrity and dimensions of the extruded calcium alginate-containing aggregated testis cells did not change (FIG. 1B) and intercellular association during culture was effectively maintained. By 10 weeks of culture, small spherical cells (7–10 µm) were apparent at the margins of encapsulated cells in culture (FIG. 1C). When encapsulated cells were dissociated, a distribution in cell size from 7 to 20 μm was observed. Cell morphology was generally spherical with apparently intact plasma membranes based on the distinct margins of individual cells (FIG. 1D). Cell morphology and integrity was similar for testis cells cultured after freezing and thawing.

Example 8

Figure 2:
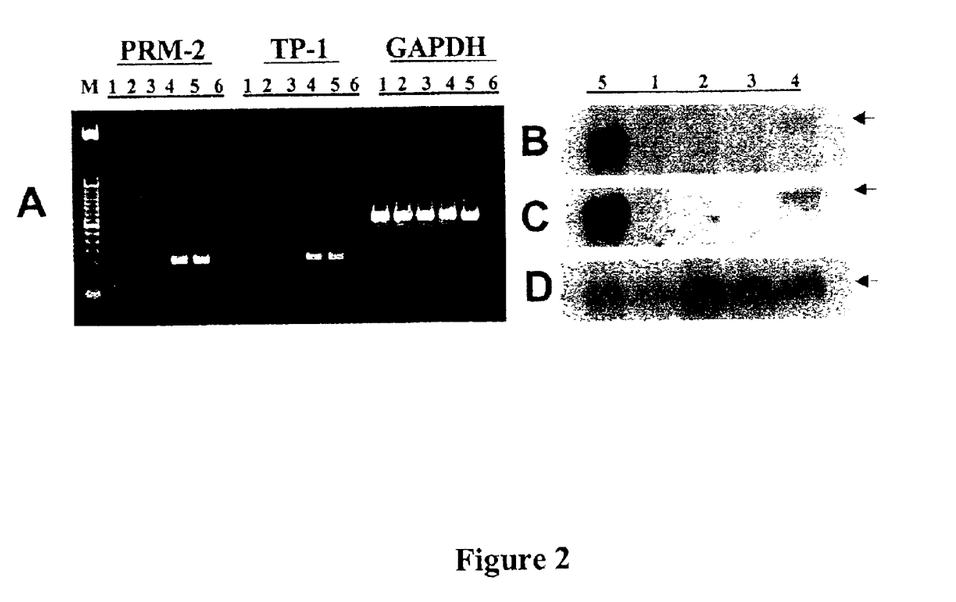
Figure 3:
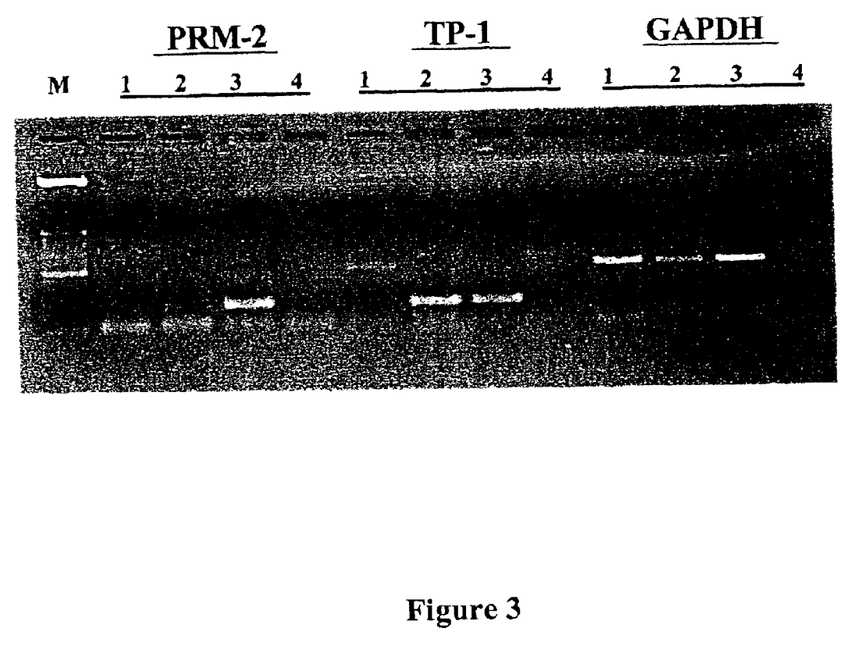
FIG. 3 illustrates the expression pattern of protamine-2 (PRM-2) (140 bp), transition protein-1 (TP-1) (150 bp), and GAPDH (379 bp) genes in frozen-thawed testis cells from a neonatal bull following culture in vitro based on RT-PCR. Lanes: M, MW marker (50 bp ladder); 1, 3 day-old testis; 2, 10-week culture; 3, adult testis; 4, negative control.

Messenger RNA Expression of PRM-2 and TP-1 Genes in Encapsulated Cell Mass Cultured in vitro Expression of PRM-2 and TP-1 by the encapsulated cells cultured for 2, 5, and 10 weeks was analyzed by RT-PCR. Testicular tissue samples from an adult and a 3-day-old bull were used as positive and negative controls, respectively, and GAPDH was included as an internal control for gene expression. Specific bands corresponding to mRNA of PRM-2 and TP-1 were detected only in samples cultured for 10 weeks and in adult testis, indicating the presence of spermatids (FIG. 2A). The detected PCR products were verified by automated nucleotide sequencing and used as templates for probes for Northern blot analysis. Frozen-thawed testis cells were also competent to develop in vitro, as similar patterns for PRM-2 and TP-1 expression were observed following culture of frozen-thawed germ cells (FIG. 3).

To confirm RT-PCR results, RNA isolated from testicular and in vitro-cultured tissue was analyzed by Northern blot hybridization with $^{32}$P-labeled probes for PRM-2 and TP-1. Transcripts of 0.47 and 0.37 kilobases (kb) were detected using probes for PRM-2 and TP-1, respectively, in samples cultured for 10 weeks and in adult testis (FIGS. 2B and 2C).

Example 9

Flow Cytometric Analysis of DNA Content in Cultured Cells

Figure 4:
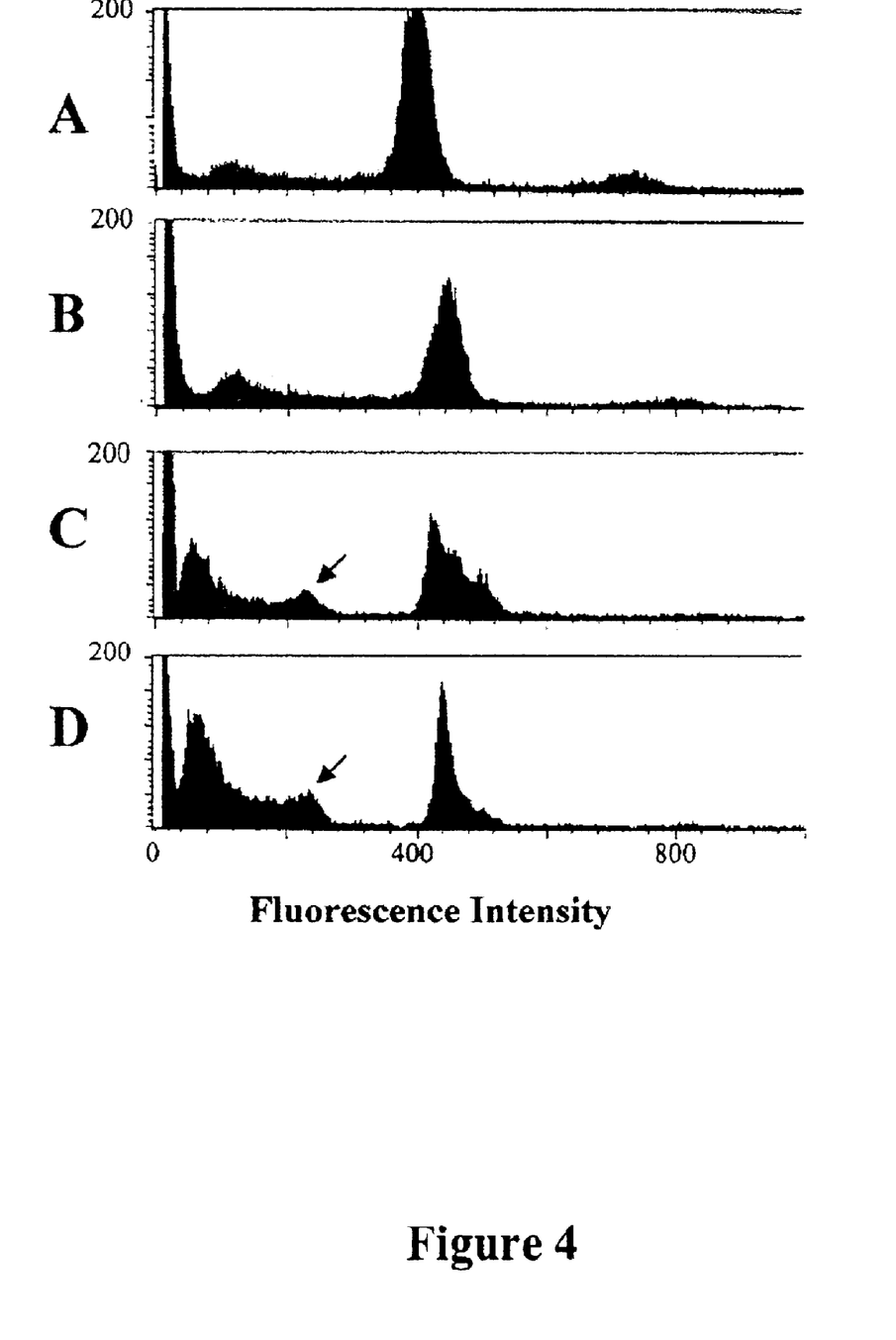
FIGS. 4A–D illustrate the frequency distribution of testis cells based on fluorescence intensity due to nuclear staining with propidium iodide. Neonatal bull testis are shown prior to culture (FIG. 4A), after 10 (FIG. 4B) and 14 (FIG. 4C) weeks of culture, and adult bull testis (FIG. 4D). The major peak contains diploid cells and the peak at half the fluorescence intensity of major peak (arrow) is haploid cells.

DNA content of individual cells was analyzed by flow cytometry after staining with propidium iodide. A major population of presumptive diploid cells based on fluorescence intensity of dispersed adult testis cells and washed, ejaculated bull sperm was detected with a relative flourescence intensity of 440 (FIG. 4). A slight shift in the distribution of cellular DNA content was detected by 10 weeks of culture and a subpopulation of testis cells with haploid DNA (relative flourescence intensity ~220) was detected in cell associations cultured after 14 weeks in vitro and in adult testis but not in 3-day-old bull testis (FIG. 4). The leading peak is attributed to fragmented cells based on microscopic observation. The distribution of cells cultured for 14 weeks in vitro had a similar flourescence intensity pattern to those from adult testis.

Example 10

Method of In vitro Spermatogenesis and Its Uses

In the present study, dissociated testis cells were first aggregated by phytohemagglutinin followed by encapsulation with calcium alginate (Adaniya et al., "First Pregnancies and Livebirths from Transfer of Sodium Alginate Encapsulated Embryos in Rodent Model," *Fertil. Steril.* 59:652–656 (1993); and Gruber et al., "Human Intervertebral Disc Cells from the Annulus: Three-Dimensional Culture in Agarose or Alginate and Responsiveness to TGF-Beta 1," *Exp. Cell Res.* 235:13–21 (1997), which are hereby incorporated by reference in their entirety) before being transferred to culture medium (FIG. 1B). Sodium alginate is a polysaccharide that forms a hydrogel when complexed with calcium and is used widely for culturing and transplanting cells, tissues, and embryos because it is non-toxic, highly permeable, biodegradable, and provides three-dimensional support (Zimmermann et al., "Hydrogel-Based Non-Autologous Cell and Tissue Therapy," *Biotechniques* 29:564–581 (2000), which is hereby incorporated by reference in its entirety). Though larger in diameter than endogenous seminiferous tubules (~200 versus ~50 μm diameter, respectively), alginate-encapsulated cell aggregates approximated the cell density and linear arrangement of native tubules (FIGS. 1B and 1C). Extruded alginate strands containing aggregated testis cells were delicate but potency and close intercellular associations were maintained throughout 14 weeks of in vitro culture (FIGS. 1B and 1C). Whether lectin-mediated aggregation and alginate encapsulation facilitated cell adhesion and the formation of specific junctional complexes observed in vivo remains to be determined.

Despite the low number of testis cells present in the long-term cultures, evidence for the progression of gonocytes to presumptive round spermatids was supported by expression of PRM-2 and TP-1 between mRNA 5 and 10 weeks of culture (35–70 days). Expression of these genes has been shown to be spermatid-specific in a variety of species (Heidaran et al., "Transcriptional and Translational Control of the Message for Transition Protein 1, a Major Chromosomal Protein of Mammalian Spermatids," *J. Biol. Chem.* 262:13309–13315 (1987); Hecht, "Regulation of 'Haploid Expressed Genes' in Male Germ Cells," *J. Reprod. Fert.* 88:679–693 (1990); Wykes et al., "Coordinate Expression of PRM1, PRM2, and TNP2 Multigene Locus in Human Testes," *DNA Cell Biol.* 14:155–161 (1995); and Nayernia et al., "Stage and Developmental Specific Gene Expression During Mammalian Spermatogenesis," *Int. J. Dev. Biol.* 40:379–383 (1996), which are hereby incorporated by reference in their entirety). Hue et al. also used stage-specific markers to describe changes in the spermatocyte and spermatid population in the postpartum rat testis between 18 and 60 days and in pubertal rat testes cultured for 20 days (Hue et al., "Meiotic Differentiation of Germinal Cells in Three-Week Cultures of Whole Cell Population from Rat Seminiferous Tubules," *Biol. Reprod.* 59:379–387 (1998), which is hereby incorporated by reference in its entirety). The appearance of spermatid-specific markers in the rat testis was coincident with the appearance of haploid germ cells. These results must be interpreted with caution, however, as evidence for spermatid development without the completion of meiosis has been presented for the mouse (Mori et al., "Completion of Meiosis is Not Always Required for Acrosome Formation in HSP70-2 Null Mice," *Biol. Reprod.* 61:813–822 (1999), which is hereby incorporated by reference in its entirety) and Drosophila (Lin et al., "Coordinate Developmental Control of the Meiotic Cell Cycle and Spermatid Differentiation in Drosophila Males," *Development* 122:1331–1341 (1996), which is hereby incorporated by reference in its entirety). Germ cell development in the present culture system has not yet been assessed for cell-specific morphological markers other than cell size.

Little change in distribution of cellular DNA content was observed in neonatal bull testis cells cultured for 10 weeks (FIG. 4) when PRM-2 was first detected. However, a peak in cells containing haploid DNA content was apparent following 14 weeks of culture, suggesting that the number of spermatids present after 10 weeks of culture was adequate to detect PRM-2/TP-1 expression by RT-PCR and Northern blotting but too low to be resolved by flow cytometric analysis. This observation is consistent with the low number of cells in culture corresponding in size to round spermatids (7–10 μm, FIG. 1D) and the relatively weak signal detected on Northern blots (FIGS. 2B and 2C). A cell peak with 4C DNA content that would provide evidence for spermatocytes in meiotic prophase is not observed. This would lead to the conclusion that meiosis is not occurring if observed only for cultured cells. However, absence of a 4C DNA peak appears to be due to dissolution of cells following permeabilization and dissociation with detergent, as the peak is absent from treated but not treated adult testis cells.

Under the present culture conditions, physiological constraints to the initiation of spermatogenesis at puberty somehow were circumvented. The timing of presumptive spermatid appearance in culture was delayed compared to the progression and duration of bovine spermatogenesis in vivo (Berndtson et al., "The Cycle of the Seminiferous Epithelium and Spermatogenesis in the Bovine Testis," *Am. J. Anat.* 140:167–180 (1974); and Johnson, "Spermatogenesis in the Bull," *Proc 16th Ann. Conf. Natl. Assoc. Anim. Breed* 15:9–27 (1994), which are hereby incorporated by reference in their entirety) but highly accelerated relative to the onset of puberty as sperm are not formed in vivo until around 6 months of age (Asdell, "Patterns of Mammalian Reproduction," New York: Cornell University Press; 1946: 597, which is hereby incorporated by reference in its entirety). Presence of testosterone and other medium components increased permeability to these components, and the intercellular associations which developed due to in vitro conditions were apparently adequate to stimulate Sertoli cell function and consequently germ cell proliferation and differentiation.

The delayed detection of haploid cells by flow cytometry compared to the initial expression of spermatid-specific mRNAs suggests that improving culture conditions or longer-term culture of neonatal testis cells may be required to increase spermatid production and initiate spermiogenesis. Additionally, initiating cultures with seminiferous tubule cells from peripuberal or adult testes using the present system of aggregation and encapsulation could enhance the appearance of and postmeiotic changes to spermatids. However, identification of appropriate probes for evaluating the progression of spermatogenesis in vitro will be required when starting with sexually mature animals to confirm that advanced germ cells did not arise simply by limited differentiation of precursor cells.

Differentiation of frozen-thawed testis cells following aggregation and encapsulation was similar to that observed for fresh, unfrozen cells as demonstrated previously following spermatogonial transplantation (Avarbock et al., "Reconstitution of Spermatogenesis from Frozen Spermatogonial Stem Cells," *Nature Med.* 2:693–696 (1996), which is hereby incorporated by reference in its entirety). General appearance of cell cultures from frozen-thawed preparations and expression of stage-specific markers during culture indicated that both germ cells and Sertoli cells survived the relatively simple freezing and thawing procedures and were competent to divide and differentiate. Developmental competence of cryopreserved germ cells has important practical ramifications for the application of IVS technology.

While recapitulating spermatogenesis in vitro will greatly facilitate mechanistic studies of the in vivo process, the primary impetus for developing an effective IVS procedure has been to generate developmentally competent haploid spermatids or sperm to be used in conjunction with ICSI or ROSI procedures in treating selected causes of male infertility (Palermo et al., "Pregnancies After Intracytoplasmic Sperm Injection of Single Spermatozoon into an Oocyte," *Lancet* 340:17–18 (1992); Van Steirteghem et al., "Use of Assisted Fertilization," *Hum. Reprod.* 8:1784–1785 (1993); and Tesarik et al., "Restoration of Fertility by In-vitro Spermatogenesis," *Lancet* 353: 555–556 (1999), which are hereby incorporated by reference in their entirety). The present study demonstrates that dissociation, reaggregation, and encapsulation of Sertoli cells and germ cells can improve long-term culture conditions such that germ cell differentiation can be achieved when starting with an infantile testis. These conditions could not only enhance current approaches to treating male factor infertility but may provide the option of preserving testicular tissue for future use from young male patients anticipating the loss of gonadal function due to chemotherapy or other treatments.

Applications of procedures presented here can also be extended to genetic modification of the germ line of domestic and laboratory animals and conservation efforts for threatened and endangered species where male fertility is an issue. Further refinement of culture conditions and characterization of Sertoli and germ cells produced in vitro are imperative to determine whether presumptive spermatids are produced by normal progression through primary spermatocytes and meiosis or an abherent differentiation during spermatocytogenesis.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of in vitro spermatogenesis comprising:
   isolating a plurality of Sertoli cells and a plurality of undifferentiated diploid germ cells from a testis of a male mammal;
   aggregating the Sertoli cells and the germ cells to yield Sertoli-germ cell aggregates;
   encapsulating the Sertoli-germ cell aggregates to yield a plurality of tubule-like structures containing both Sertoli cells and germ cells;
   transferring the tubule-like structures to a culture medium; and
   culturing the tubule-like structures under conditions effective to allow the Sertoli cells and the germ cells to interact, whereby the germ cells progress through spermatocytogenesis and meiosis to produce a plurality of differentiated haploid spermatids.

2. The method according to claim 1, wherein the mammal is selected from the group consisting of a human, a bovine, a porcine, and a rodent.

3. The method according to claim 1, wherein the male mammal is selected from the group consisting of a neonatal male, a juvenile male, a peri-pubertal male, and an adult male.

4. The method according to claim 1, wherein the male mammal is a neonatal bovine ranging in age from 1 to 5 days old.

5. The method according to claim 4, wherein the neonatal bovine is 3 days old.

6. The method according to claim 1, wherein the male mammal is a peri-pubertal bovine.

7. The method according to claim 1, wherein the male mammal is an adult bovine.

8. The method according to claim 1, wherein the undifferentiated diploid germ cell is a gonocyte.

9. The method according to claim 1, wherein said isolating comprises:

decapsulating a portion of the testis to yield exposed parenchyma tissue containing a plurality of seminiferous tubules containing Sertoli cells and germ cells;

dissociating the Sertoli and germ cells from the seminiferous tubules using a first enzyme solution to yield a mixture comprising peritubular cells, dissociated Sertoli cells, dissociated germ cells, and dissociated seminiferous tubules;

separating the dissociated Sertoli cells, germ cells, and seminiferous tubules from the peritubular cells; and incubating the dissociated Sertoli cells, germ cells, and seminiferous tubules in a second enzyme solution which assists in releasing the dissociated Sertoli and germ cells from the seminiferous tubules.

10. The method according to claim 9, wherein said decapsulating comprises:

manually decapsulating a portion of tunica albuginea of the testis.

11. The method according to claim 9, wherein said first enzyme solution comprises collagenase, DNase I, soybean trypsin inhibitor, and hyaluronidase in $Ca^{++}$, $Mg^{++}$-free PBS.

12. The method according to claim 9, wherein said second enzyme solution comprises collagenase, DNase I, soybean trypsin inhibitor, and hyaluronidase in $Ca^{++}$, $Mg^{++}$-free PBS.

13. The method according to claim 1 further comprising:

storing the isolated Sertoli cells and germ cells prior to said aggregating.

14. The method according to claim 13 further comprising:

storing the isolated Sertoli and germ cells in liquid nitrogen prior to said aggregating and thawing to yield a frozen-thawed suspension of isolated Sertoli cells and germ cells.

15. The method according to claim 1, wherein the said aggregating is carried out using a chemical aggregating agent.

16. The method according to claim 15, wherein the chemical aggregating agent is phytohemagglutinin.

17. The method according to claim 1, wherein said encapsulating is carried out by a chemical encapsulating agent.

18. The method according to claim 17, wherein the chemical encapsulating agent is sodium alginate.

19. The method according to claim 1, wherein the culture medium comprises HEPES-buffered DMEM/F12 medium supplemented with insulin-transferrin-selenium solution, vitamin C, vitamin E, retinoic acid, retinol, pyruvate, bovine FSH, testosterone, antibiotic-antimycotic solution, and bovine calf serum.

20. The method according to claim 19, wherein the culturing of the tubule-like structures is carried out in the culture medium for up to 14 weeks at a temperature in a humidified atmosphere of about 5% carbon dioxide in air.

21. The method according to claim 20, wherein culturing is carried out in the culture medium for a period of 2, 5, 10, or 14 weeks.

* * * * *